(12) United States Patent
Mallet et al.

(10) Patent No.: US 8,431,119 B2
(45) Date of Patent: Apr. 30, 2013

(54) PHARMACEUTICAL COMPOSITIONS AND UTILIZATION THEREOF PARTICULARLY FOR THE TREATMENT OF NEURODEGENERATIVE DISEASES

(75) Inventors: Jacques Mallet, Paris (FR); Frederic Revah, Paris (FR); Jean-Marie Stutzmann, Villecresnes (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 11/842,983

(22) Filed: Aug. 22, 2007

(65) Prior Publication Data

US 2008/0032284 A1 Feb. 7, 2008

Related U.S. Application Data

(60) Division of application No. 09/578,453, filed on May 26, 2000, now Pat. No. 7,273,854, which is a continuation of application No. 08/624,469, filed as application No. PCT/FR94/01142 on Sep. 29, 1994, now abandoned.

(30) Foreign Application Priority Data

Oct. 4, 1993 (FR) ...................................... 93 11774

(51) Int. Cl.
*A01N 63/00* (2006.01)
*A01N 43/04* (2006.01)
*C12N 15/00* (2006.01)
*A61K 31/70* (2006.01)

(52) U.S. Cl.
USPC .............. 424/93.2; 435/455; 435/6.1; 514/55

(58) Field of Classification Search ........................ None
See application file for complete search history.

(56) References Cited

U.S. PATENT DOCUMENTS

| 5,087,617 | A | 2/1992 | Smith |
|---|---|---|---|
| 5,474,935 | A | 12/1995 | Chatterjee et al. |
| 5,532,220 | A | 7/1996 | Lee et al. |
| 5,565,334 | A | 10/1996 | Kufe et al. |
| 5,624,803 | A | 4/1997 | Noonberg et al. |
| 5,641,749 | A | 6/1997 | Yan et al. |
| 5,641,750 | A | 6/1997 | Louis |
| 5,672,344 | A | 9/1997 | Kelley et al. |
| 5,700,657 | A | 12/1997 | Beaudry et al. |
| 5,716,826 | A | 2/1998 | Gruber et al. |
| 5,731,172 | A | 3/1998 | Saito et al. |
| 6,017,524 | A | 1/2000 | Roth et al. |
| 6,261,834 | B1 | 7/2001 | Srivastava |

FOREIGN PATENT DOCUMENTS

| WO | WO 91/18088 | 11/1991 |
|---|---|---|
| WO | WO 92/05272 | 4/1992 |
| WO | WO 92/19732 | 11/1992 |

OTHER PUBLICATIONS

Choi, et al. (1987) Glutamate Neurotoxicity in Cortical Cell Culture. The Journal of Neuroscience, v.7(2):357-68.*
Le Gal la Salle, et al (1993) An Adenovirus Vector for Gene Transfer Into Neurons and Glia in the Brain. Science, v.259:988-90.*
El-Deiry, et al. (1992) Definition of a consensus binding site for p53, Nature Genetics, v.1:45-9.*
Holt, J. (1991) Cutting the Chain of Command: Specific Inhibitors of Transcription, Antisense Research and Development, v.1:365-9.*
International Search Reprot WO95/09916 dated Apr. 13, 1995.

* cited by examiner

*Primary Examiner* — Jennifer Pitrak McDonald
(74) *Attorney, Agent, or Firm* — J. Darrell Fontenot

(57) ABSTRACT

The present invention relates to pharmaceutical compositions that act on the p53 protein or its gene and methods of use for the treatment of neurodegenerative diseases.

2 Claims, No Drawings

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial
<220> FEATURE:
<223> OTHER INFORMATION: antisense capable of reducing levels of
      expression of p53

<400> SEQUENCE: 1
cgactgtgaa tcctccat                                              18

<210> SEQ ID NO 2
<211> LENGTH: 20
<212> TYPE: DNA
<213> ORGANISM: Artificial
<220> FEATURE:
<223> OTHER INFORMATION: site for binding of p53

<400> SEQUENCE: 2
ggacatgccc gggcatgtcc                                            20
```

PHARMACEUTICAL COMPOSITIONS AND UTILIZATION THEREOF PARTICULARLY FOR THE TREATMENT OF NEURODEGENERATIVE DISEASES

The present invention relates to pharmaceutical compositions and their use, especially in the treatment of neurodegenerative diseases. It relates more particularly to the use of compounds acting on the p53 protein or on its gene for the preparation of a pharmaceutical composition intended for the treatment of neurodegenerative diseases.

The p53 gene encodes a nuclear protein of 53 kDa. The wild-type gene encoding the native p53 has an antioncogenic activity [for a review, see for example Oren, FASEB J. 6 (1992) 3169]. In particular, the wild-type p53 protein is capable of inhibiting the formation of transformation foci in the fibroblasts of rodents infected with various combinations of oncogenes. The form mutated by deletion and/or mutation of this gene is on the contrary involved in the development of most human cancers [Baker et al., Science 244 (1989) 217]. Its mutated forms are also capable of cooperating with the ras oncogenes to transform murine fibroblasts. For this reason, the p53 protein or its gene have been widely studied as targets for the treatment of cancers. Moreover, Chopp et al. (Biochem. Biophys. Res. Com 182 (1992) 1201) have described a p53 expression in ischaemic mouse brain. However, nothing indicates in these results if this expression constitutes a cause of neurodegeneration, or a parallel phenomenon. Furthermore, no therapeutic approach is envisaged or suggested in this document.

The present invention partially results from the demonstration that the p53 protein constitutes a mediator of neuronal degeneration. It also results from the demonstration that the use of compounds capable of at least partially inhibiting the activity of p53 protein can make it possible to block the process of neuronal death.

In order to study the molecular mechanisms of neuronal degeneration, the Applicant has used, as a model, mice in which the expression of the p53 gene has been inactivated [Donehower et al., Nature 356 (1992) 215]. Irreversible focal ischaemia experiments were performed on these mice, and the volumes of infarct were compared with those observed in control wild-type mice (same strain, same sex, same age, same supplier). The results obtained showed a statistically significant decrease of 20% in the volumes of infarct after ischaemia in mice not expressing the p53 gene (cf. examples). Furthermore, the Applicant has also demonstrated that the use of anti-p53 antisense makes it possible to reduce the glutamate-induced death on cortical cell cultures. These results demonstrate that the p53 protein plays a mediating role in neuronal degeneration, an observation which has never been reported in the prior art, and that a control of the activity of this protein makes it possible to combat neuronal death. The p53 protein, its gene and all the factors capable of interacting with it therefore constitute new pharmacological targets in the treatment of neurodegenerative processes. The invention therefore consists, in part, in the use of compounds capable of at least partially blocking the activity of p53 for the treatment of neurodegenerative diseases.

A first subject of the present invention consists in the use of a compound which at least partially inhibits the activity of the p53 protein for the preparation of a pharmaceutical composition intended for the treatment and/or the prevention of neurodegenerative diseases.

The compounds which at least partially inhibit the activity of the p53 protein for the purposes of the present invention may be compounds which act (i) on the synthesis of p53, at the transcriptional, translational or post-translational levels, or (ii) on the binding of p53 to DNA.

Among the compounds which act on the synthesis of the p53 protein, there may be mentioned the antisense nucleotide sequences capable of reducing or of suppressing the expression of p53, at the transcriptional or translational level.

Such sequences may indeed be directed against the p53 mRNA and act on its translation into protein: they may be oligonucleotides (synthetic, chemically modified and the like, as described for example in Applications EP 092 574, EP 231 495, WO 92/03568; WO 91/13080 and the like) or DNA sequences encoding RNAs capable of selectively interacting with the p53 mRNA, according to the technique described for example in application EP 140 308.

Such sequences may also be directed against the gene encoding p53 and act on its transcription into RNA. More particularly, these sequences may be directed against coding regions of the gene (p53 structural gene), or against noncoding regions: regions regulating transcription, exons and the like. Such sequences can be prepared under the conditions described for example in EP 558 634, WO 91/06626, WO 92/10590, WO 93/10820 and the like).

Among the compounds which act on the binding of p53 to DNA, there may be mentioned more particularly p53 antagonists, or proteins capable of interacting with p53 and of thus modulating its DNA-binding activity. In this regard, there may be mentioned the negative dominant mutants of p53 consisting essentially of inactive mutated form, which are capable of entering into competition with the wild-type protein for the interaction with DNA. Such mutants are for example the p53Val135 mutant, or other forms described for example in Michalovitz et al. [J. Cell. Bioch. 45 (1991) 22]. They can be used as such, but, preferably, they are used within the framework of the present invention in the form of genetic constructs capable of expressing these mutants in vivo. Other compounds capable of at least partially inhibiting the binding of p53 to DNA consist of double-stranded nucleic acids reproducing the site for binding of p53 to DNA [El-Deiry et al., Nature 1 (1992) 45; Kern et al., Science 252, 1708; Friedman et al., PNAS 90 (1993) 3319]. The Applicant has indeed shown that such nucleic acids were capable of complexing the transcription factors present in the cells, of preventing them from attaching to their endogenous sites, and thus, of blocking their transcriptional activity.

In a preferred mode, the compound used within the framework of the present invention is a double-stranded nucleic acid comprising all or part of the site for the binding of p53 to DNA. More preferably, the nucleic acid comprises all or part of the sequence SEQ ID No. 2 or an active variant thereof. The term active variant designates, for the purposes of the invention, any variant of the sequence SEQ ID No. 2 which has conserved the properties of attachment to the p53 protein. Such variants can be obtained by mutation, deletion, substitution and/or addition of bases to the sequence SEQ ID No. 2, followed by verification in vitro of the binding activity.

In another preferred mode, the compound used within the framework of the present invention is a nucleic acid encoding a mutated form of the p53 protein capable of antagonizing the activity thereof.

Still in a preferred mode, the compound used within the framework of the present invention is an antisense nucleic acid capable of reducing the levels of expression of the p53 protein, at the transcriptional or translational level. More preferably, it is a DNA encoding an antisense ribonucleic acid capable of inhibiting the translation of the p53 cellular mRNA. Such an antisense is represented on the sequence SEQ ID No. 1.

The nucleic acid can be used as such, for example after injection into man or animals, in order to induce a protection or to treat neuronal degeneration. In particular, it can be injected in naked DNA form according to the technique described in application WO 90/11092. It can also be administered in complexed form, for example with DEAE-dextran [Pagano et al., J. Virol. 1 (1967) 891], with nuclear proteins [Kaneda et al., Science 243 (1989) 375], with lipids [Felgner et al., PNAS 84 (1987) 7413], in the form of liposomes [Fraley et al., J. Biol. Chem. 255 (1980) 10431], and the like.

Preferably, the nucleic acid used within the framework of the invention forms part of a vector. The use of such a vector makes it possible, indeed, to enhance the administration of the nucleic acid into the cells to be treated, and also to increase its stability in the said cells, which makes it possible to obtain a lasting inhibitory effect. Furthermore, it is possible to introduce several nucleic acid sequences into the same vector, which also increases the efficiency of the treatment.

The vector used may be of various origins, as long as it is capable of transforming animal cells, preferably human nerve cells. In a preferred embodiment of the invention, a viral vector is used which may be chosen from adenoviruses, retroviruses, adeno-associated viruses (AAV), the herpes virus, and the like.

In this regard, the subject of the present invention is also any recombinant virus comprising, inserted into its genome, a nucleic acid encoding a mutated form of the p53 protein capable of antagonizing the activity thereof, and/or a nucleic acid comprising all or part of the site for binding of p53 to DNA and/or an antisense nucleic acid capable of reducing the levels of expression of the p53 protein, at the transcriptional or translational level.

The recombinant virus according to the invention may be chosen from adenoviruses, retroviruses, adeno-associated viruses and the like. Preferably, it is a virus capable of infecting the nerve cells, such as especially an adenovirus. Vectors derived from adenoviruses, retroviruses or AAVs incorporating heterologous nucleic acid sequences have been described in the literature [Akli et al., Nature Genetics 3 (1993) 224; Stratford-Perricaudet et al., Human Gene Therapy 1 (1990) 241; EP 185 573, Levrero et al., Gene 101 (1991) 195; Le Gal la Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO91/18088].

Advantageously, the recombinant virus according to the invention is a defective virus. The term "defective virus" designates a virus incapable of replicating in the target cell. Generally, the genome of the defective viruses used within the framework of the present invention therefore lacks at least the sequences necessary for the replication of the said virus in the infected cell. These regions may be either removed (completely or in part), or made nonfunctional, or substituted by other sequences and especially by the nucleic acid. Preferably, the defective virus conserves nevertheless the sequences of its genome which are necessary for the encapsulation of the viral particles.

It is particularly advantageous to use the nucleic sequences of the invention in a form incorporated into a defective recombinant adenovirus.

There are, indeed, various adenovirus serotypes whose structure and properties vary somewhat, but which are not pathogenic for man, and especially non-immunodepressed subjects. Moreover, these viruses do not integrate into the genome of the cells which they infect, and may incorporate large fragments of exogenous DNA. Among the various serotypes, the use of the type 2 or 5 adenoviruses (Ad 2 or Ad 5) is preferred within the framework of the present invention. In the case of Ad 5 adenoviruses, the sequences necessary for the replication are the E1A and E1B regions.

A specific embodiment of the invention consists in a vector, especially a viral vector, comprising at least two nucleic acids as defined above.

The defective recombinant viruses of the invention can be prepared by homologous recombination between a defective virus and a plasmid carrying, inter alia, the nucleic acid sequence as defined above [Levrero et al., Gene 101 (1991) 195; Graham, EMBO J. 3(12) (1984) 2917]. The homologous recombination occurs after co-transfection of the said viruses and plasmid into an appropriate cell line. The cell line used should preferably (i) be transformable by the said elements, and (ii) comprise the sequences capable of complementing the genome part of the defective virus, preferably in integrated form in order to avoid risks of recombination. By way of example of a line which can be used for the preparation of defective recombinant adenoviruses, there may be mentioned the human embryonic kidney line 293 [Graham et al., J. Gen. Virol. 36 (1977) 59] which contains especially, integrated into its genome, the left-hand part of the genome of an Ad5 adenovirus (12%). By way of example of a line which can be used for the preparation of defective recombinant retroviruses, the CRIP line may be mentioned [Danos and Mulligan, PNAS 85 (1988) 6460].

Next, the viruses which have multiplied are recovered and purified according to conventional molecular biological techniques.

The subject of the present invention is also a pharmaceutical composition comprising at least one recombinant virus as defined above.

The pharmaceutical compositions of the invention can be formulated for topical, oral, parenteral, intranasal, intravenous, intramuscular, subcutaneous or intraocular administration and the like.

Preferably, the pharmaceutical compositions contain pharmaceutically acceptable vehicles for an injectable formulation. They may be in particular saline solutions (monosodium or disodium phosphate, sodium, potassium, calcium or magnesium chloride and the like, mixtures of such salts), sterile solutions, isotonic solutions or dry compositions, especially freeze-dried compositions, which, upon addition, depending on the case, of sterilized water or of physiological saline, allow the constitution of injectable solutions.

The doses of nucleic acids (sequence or vector) used for the administration can be adjusted according to various parameters, and especially according to the mode of administration used, the relevant pathology, the nucleic acid to be expressed, or alternatively the desired duration of the treatment. In general, as regards the recombinant viruses according to the invention, these are formulated and administered in the form of doses of between $10^4$ and $10^{14}$ pfu/ml, and preferably $10^6$ to $10^{10}$ pfu/ml. The term pfu ("plaque forming unit") corresponds to the infectious power of a virus solution, and is determined by infecting an appropriate cell culture, and measuring, generally after 48 hours, the number of plaques of infected cells. The techniques for the determination of the pfu titre of a viral solution are well documented in the literature.

Such pharmaceutical compositions can be used in man, for the treatment and/or prevention of neurodegenerative diseases, and in particular for the treatment and/or the prevention of neuronal degeneration associated with ischaemia, hypoxia, anoxia, hypoglycaemia, epileptic fits or alternatively cerebral and spinal traumas, or for the treatment and/or the prevention of Huntington's chorea, Alzheimer's disease, Parkinson's disease or amyotrophic lateral sclerosis.

The present invention will be described more fully with the aid of the following examples which should be considered as illustrative and nonlimiting.

LEGEND TO THE FIGURES

FIG. 1: Inhibition of cell death induced by glutamate on primary cultures of cortical neurones by an anti-p53 antisense nucleic acid.

GENERAL CLONING TECHNIQUES

The methods conventionally used in molecular biology, such as preparative extractions of plasmid DNA, centrifugation of plasmid DNA in caesium chloride gradient, agarose or acrylamide gel electrophoresis, purification of DNA fragments by electroelution, phenol or phenol-chloroform extraction of proteins, ethanol or isopropanol precipitation of DNA in saline medium, transformation in *Escherichia coli* and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

The pBR322- and pUC-type plasmids and the phages of the M13 series are of commercial origin (Bethesda Research Laboratories).

For the ligations, the DNA fragments can be separated according to their size by agarose or acrylamide gel electrophoresis, extracted with phenol or with a phenol/chloroform mixture, precipitated with ethanol and then incubated in the presence of phage T4 DNA ligase (Biolabs) according to the recommendations of the supplier.

The filling of the protruding 5' ends can be performed with the Klenow fragment of *E. coli* DNA polymerase I (Biolabs) according to the specifications of the supplier. The destruction of the protruding 3' ends is performed in the presence of phage T4 DNA polymerase (Biolabs) used according to the recommendations of the manufacturer. The destruction of the protruding 5' ends is performed by a controlled treatment with S1 nuclease.

Site-directed mutagenesis in vitro by synthetic oligodeoxynucleotides can be performed according to the method developed by Taylor et al. [Nucleic Acids Res. 13 (1985) 8749-8764] using the kit distributed by Amersham.

The enzymatic amplification of the DNA fragments by the so-called PCR technique [Polymerase-catalyzed Chain Reaction, Saiki R. K. et al., Science 230 (1985) 1350-1354; Mullis K. B. and Faloona F. A., Meth. Enzym. 155 (1987) 335-350] can be performed using a DNA thermal cycler (Perkin Elmer Cetus) according to the specifications of the manufacturer.

The verification of the nucleotide sequences can be performed by the method developed by Sanger et al. [Proc. Natl. Acad. Sci. USA, 74 (1977) 5463-5467] using the kit distributed by Amersham.

EXAMPLES

Example 1

Reduction in the Volume of Infarct in Mice Made Ischaemic by Suppression of the p53 Gene This example describes the effect of the suppression of the p53 gene on the volume of infarct in mice made ischaemic. For that, ischemias were induced in mice by occlusion of the middle cerebral artery, and the volumes of infarct were determined and then compared.

Procedure: The animals (C57/Blc male mice 9 to 12 weeks old, Genpharm, Denmark; wild-type homozygots or Δp53) were anaesthetized in a mixture of oxygen, nitrous oxide and 1.8% halothane, and maintained under these conditions during the entire surgical procedure. The rectal temperature is maintained at 37° C.+/−0.5 by a heating cover. The left middle cerebral artery was then cauterized by electrocoagulation by means of a bipolar clip. The wound was then stitched up and the animals placed in a room at 30° C. for 24 hours, with food and drink being available ad libitum. After 24 hours, the animals were sacrificed by decapitation. The brains were removed, immersed in an isopentane bath at −30° C. and then stored at −80° C. 40 μm histological sections were then made in a cryostat at −20° C. at the rate of one section every 500 μm, from the appearance of the infarction until it disappeared. These sections were then stained with Cresyl violet. The volume of the infarction is determined by image analysis. The statistical analysis is performed by means of Student's t test for independent groups, after verification of the homogeneity of the various values. In the case where the various values were not homogeneous, the Wilcoxon's nonparametric test was used.

Results: The results obtained are presented in the table below.

|  | P53 mice | Control mice |
|---|---|---|
| Total number of animals tested | 45 | 46 |
| Mean weight (g) | 25.73 | 25.44 |
| Mean temperature (° C.) | 36.80 | 37.01 |
| Mean volume of infarct (mm$^3$) | 24.95 +/− 1.81 | 31.54 +/− 1.86 |

These results show a reduction of the order of 20% in the volumes of infarct after ischaemia in the mice not expressing the p53 gene. These results therefore demonstrate that a suppression of p53 activity makes it possible to reduce neuronal degeneration.

Example 2

Inhibition of Cell Death Induced by Glutamate of Primary Cultures of Cortical Neurones by an Anti-p53 Antisense Nucleic Acid This example describes the effect of an anti-p53 antisense nucleic acid on death induced by glutamate on embryonic rat cortical neurones, in primary culture.

Glutamate is the principal neurotransmitter exciting the central nervous system. However, exposure to glutamate for abnormally long periods, or to concentrations higher than the physiological concentrations can cause a neuronal toxicity designated by the term excitotoxicity [Olney Adv. Exp. Med. Biol. 203 (1986) 631]. Numerous experimental arguments suggest that this type of toxicity contributes to the neuronal degeneration associated with ischaemia, hypoxia, hypoglycaemia, epileptic fits or alternatively to cerebral traumas [Choi, J. Neurobiol. 23 (1992). 1261]. The excitotoxicity is also thought to be involved in the pathogenesis of diseases such as Huntington's chorea [Young et al., Science 241 (1988) 981] and Alzheimer's disease [Koh et al., Brain Res. 533 (1990) 315; Mattson et al.; J. Neurosci. 12 (1992) 376]. This example shows that the toxic effect of glutamate is partly inhibited in the presence of an antisense nucleic acid capable of reducing the levels of expression of the p53 protein.

Preparation and sequence of the antisense nucleic acid: The antisense oligonucleotide was synthesized by means of an automatic nucleotide synthesizer (Maniatis). The sequence of the oligonucleotide is as follows: 5'-CGACTGT-GAATCCTCCAT-3' (SEQ ID No. 1).

Study of inhibition: Embryonic Wistar rat cortex cells (E17) were isolated according to the method of Dichter [Brain Res. 149 (1978) 279], cultured in 6-well Costar plates (35 min; density $6 \times 10^5$ cells/plate), in DMEM medium (Dulbecco's Modified Eagle Medium) containing 10 µg/ml insulin, 10 µg/ml transferrin, 10 ng/ml sodium selenite, 10 nM progesterone, 1 nM triiodothyronine, and stored in an oven (37° C., 5% CO2). 2 µM anti-p53 antisense nucleic acid described above were then added to the cultures, during the inoculation, and then on days 1 and 2. The glutamate (5 mM) was administered on day 2, at the same time as the anti-p53 antisense nucleic acid. The toxicity induced by the glutamate was determined after 24 hours of culture, by measuring the mitochondrial activity according to the technique described by Manthorpe et al. [Dev. Brain. Res. 25 (1986) 191].

The results obtained are presented in FIG. 1. They show clearly that the anti-p53 antisense nucleic acid is capable of reducing by about 25% the toxicity induced by glutamate.

What is claimed:

1. A method for determining whether a nucleic acid antagonizes the activity of the p53 protein, comprising the steps of:
   (a) generating a recombinant defective virus selected from the group consisting of adenovirus, adeno-associated virus and herpes virus comprising said nucleic acid; wherein said nucleic acid is selected from the group consisting of: (i) a nucleic acid encoding a mutated form of p53 which antagonizes wild-type p53-mediated neuronal cell degradation in vitro; and (ii) a nucleic acid that reproduces the site of binding of p53 to DNA;
   (b) treating a culture of neuronal cells sensitive to glutamate-induced excitotoxicity with said defective virus so that said defective virus enters said neuronal cells,
   (c) adding an excitotoxic amount of glutamate to the culture medium of said neuronal cells;
   (d) comparing the amount of excitotoxicity measured in said neuronal cells with the amount of excitotoxicity measured in neuronal cells which were not treated with said nucleic acid,
   wherein a decrease in excitotoxicity measured in the neuronal cells treated with said nucleic acid as compared to the excitotoxicity measured in the neuronal cells not treated with said nucleic acid is indicative that said nucleic acid at least partially inhibits the activity of the p53 protein.

2. The method according to claim 1, wherein the neuronal cells are embryonic rat cortical neurons.

* * * * *